United States Patent [19]

Conner

[11] 4,333,920
[45] Jun. 8, 1982

[54] BENZALPHTHALIDES AND BROAD SPECTRUM SUN SCREENS

[75] Inventor: Donald E. Conner, Clifton, N.J.

[73] Assignee: Van Dyk & Company, Inc., Belleville, N.J.

[21] Appl. No.: 42,013

[22] Filed: May 24, 1979

Related U.S. Application Data

[63] Continuation-in-part of Ser. No. 14,598, Feb. 23, 1979, abandoned.

[51] Int. Cl.³ .............................................. A61K 7/42
[52] U.S. Cl. ...................................... 424/59; 424/174; 542/441
[58] Field of Search ................... 260/343.3 R; 424/59

[56] References Cited

U.S. PATENT DOCUMENTS

| | | | |
|---|---|---|---|
| 1,941,474 | 1/1934 | Jaeger | 260/343.3 R |
| 2,088,633 | 8/1937 | Bousquet et al. | 260/343.3 R |
| 2,475,150 | 7/1949 | Mowry | 260/343.3 X |
| 2,489,972 | 11/1949 | Mowry et al. | 260/343.3 X |
| 2,810,731 | 10/1957 | Shakleton | 260/343.3 R |
| 2,890,225 | 6/1959 | Gregory | 424/59 X |
| 3,052,721 | 9/1962 | Bernstein et al. | 260/343.3 X |
| 3,116,324 | 12/1963 | Dolliver | 260/343.3 X |
| 3,641,133 | 2/1972 | Galantay et al. | 260/343.3 X |
| 3,663,378 | 5/1972 | Brown | 260/343.3 |
| 3,712,947 | 1/1973 | Theimer | 424/59 |
| 3,770,730 | 11/1973 | Brown | 260/343.3 X |
| 3,927,018 | 12/1975 | Houlihan | 260/343.3 R |

FOREIGN PATENT DOCUMENTS 769718 3/1957 United Kingdom ............. 260/343.3

OTHER PUBLICATIONS

Graf et al., Helv. Chim. Acta., 1959, vol. 42, pp. 1085 to 1087 & 1090 to 1101.

Capisarow et al., Chem. Abs., 1915, vol. 9, pp. 2519 and 2520.

Giese et al., J. of Amer. Pharm. Assoc., 1 to 12/1950, pp. 30 to 36.

*Primary Examiner*—Dale R. Ore
*Attorney, Agent, or Firm*—L. Chasan

[57] ABSTRACT

Compositions containing a benzalphthalide, i.e. benzalphthalide or a substituted benzalphthalide, are very effective broad spectrum sun screens. They are prepared by reacting substituted or unsubstituted phthalic anhydride with the corresponding substituted or unsubstituted phenyl acetic acid.

18 Claims, No Drawings

BENZALPHTHALIDES AND BROAD SPECTRUM SUN SCREENS

CROSS-REFERENCE TO RELATED APPLICATIONS

This application is a continuation in part of Ser. No. 14,598, filed Feb. 23, 1979, now abandoned.

FIELD OF THE INVENTION

Extensive studies have been made of the ultraviolet radiation of sunlight and skylight reaching the surface of the earth and the effects of such radiation on the human skin. It has been established that the radiation between 290 nanometers and 315 nanometers produces substantially all of the burning, or erythemal energy, and a substantial portion of the tanning energy, while the between 315 nanometers and 400 nanometers promotes incident tanning. The different intensities and the erythemal and tanning effectiveness of the various wave lengths within these ranges have been established and methods have been determined for calculating accurately their effects on normal untanned skin.

Approximately 76% of the physiological tanning potential of sunlight is found in the ultraviolet range between 290 nanometers and 315 nanometers, the so called erythema area; the balance is found in the range between 315 nanometers and 400 nanometers, the so called tanning area. The erythemal limitations necessarily control the amount of tanning which may be obtained from ultraviolet in the erythemal area, but there is no limitation on the availability of tanning from the ultraviolet in the incident tanning area since it has no appreciable erythemal effect.

It is becoming increasingly apparent that ultraviolet in the tanning area can also have detrimental effects on skin health. Accordingly, the need has developed for effective broad spectrum sun screens.

For human application, sun screens are incorporated in various cosmetic oil carriers, i.e. oily solutions, oil lotions, and creams. Additionally, a material such as dihydroxyacetone may be incorporated in the medium to provide an artificial "tanning", i.e. pigmentation of the skin which resembles natural melanin pigmentation in appearance only.

Therefore, a practical, all-purpose ultraviolet or sun screen should:

Provide high screening efficiency;

Be capable of being readily incorporated in the various oil and alcoholic media used to apply them to human skin, and remain stable, effective and cosmetically acceptable therein under all conditions normally encountered in commercial use;

Be resistant to oxidation by air and stable on exposure to both ultraviolet and visible radiation under all normal conditions of storage, application and use.

SUMMARY OF THE INVENTION

It has now been found that benzalphthalides, i.e. benzalphthalide and substituted benzalphthalides are very effective broad spectrum sun screens.

DETAILED DESCRIPTION

The active chemicals of this invention are benzalphthalides, i.e. benzalphthalide, or a substituted benzalphthalide corresponding to the formula

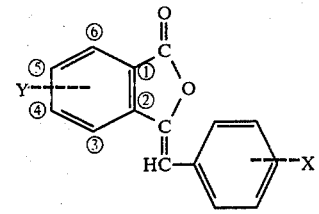

wherein X and Y are selected from the group consisting of hydrogen, methyl, ethyl, methoxy, hydroxy and chloro. X and Y can thus be the same or different.

The efficacy of the X substituted benzalphthalides are determined in an empiric manner. Thus, the four-nitro benzalphthalide derivative is ineffective, and the 4-amino and 4-dimethyl amino derivatives are also cosmetically unsatisfactory as a sun screen. Conversely, the position of the substituents of the particularly useful listed compounds can be important because shifting the position gives less desirable results.

The Y can be in the 3 through 6 position. When an asymmetrical phthalic anhydride is reacted with unsubstituted or substituted phenyl acetic acids, a mixture of isomers is obtained. In the laboratory some of these mixtures have been separated, but in practice the mixture would not be separated but used in total.

Particularly preferred compounds are 4-chlorobenzalphthalide, 4-methylbenzalphthalide, 3-methoxybenzalphthalide, and benzal-3-methyl phthalide and 3-methoxy benzal-3-methyl phthalide. 4-hydroxybenzalphthalide is also useful.

The materials of this invention are in general prepared from the substituted or unsubstituted phthalic anhydride and the corresponding substituted or unsubstituted phenyl acetic acid utilizing conveniently sodium acetate as the catalyst.

The cosmetic oil carriers are as stated those known to the trade, e.g. mineral, vegetable and animal oils, and isopropyl myristate. The active phthalide component is utilized in an amount sufficient to provide the desired protection up to the limit of solubility of the carrier. Typical ranges employed in the carrier are from about 1 to about 8 wt.%, usually 1 to about 5 wt.%.

This invention, product workup, and properties of the materials will be better understood by reference to the following examples.

EXAMPLE 1

Benzalphthalide 400 g phthalic anhydride
440 g phenyl acetic acid
5.2 g sodium acetate (fused)

The above materials were heated in a 2 liter flask, fitted with a water trap, thermometer, nitrogen sparger and mechanical stirrer. The temperature was brought up to 240° C. over a 1 hr. period and kept there for an additional 2 hrs. During this heating period 42 ml of water was collected. After cooling the batch to 90° C., 1000 ml of ethanol was slowly added. Heat was again applied. After refluxing for 30 min. the solution was allowed to cool to below reflux temperature and then transferred to a 1000 ml beaker where it crystalized upon cooling overnight.

After filtration and on drying 389 g of yellow product was obtained.

After a second crystallization from 1000 ml of ethanol, containing 2% carbon, 261 g of very light yellow crystals, having a melting point of 99°–100° C., was obtained.

| Ultraviolet Spectra Data | Isopropanol Solvent |
| --- | --- |
| $\lambda_{max}$ = 295 nanometers | K = 101.6 |
| $\lambda_{max}$ = 308 nanometers | K = 94.2 |
| $\lambda_{max}$ = 340 nanometers | K = 94.4 |

| Concentration | Erythemal Transmission | Tanning Transmission |
| --- | --- | --- |
| 1% | 11.7% | 19.7% |
| 3% | 0.2% | 2.8% |
| 4% | 0.002% | 1.6% |

EXAMPLE 2

4-Chlorobenzalphthalide 20.5 g (0.12 mole) 4-chlorophenyl acetic acid
14.8 g (0.1 mole) phthalic anhydride
0.2 g Fused sodium acetate Above mixture was heated at 240° C. for 3 hrs.; 1.5 ml of water was recovered. Solution was cooled to 85° C. and added to 500 ml isopropanol. After crystallization was completed, the solids were filtered off and recrystallized from 300 ml isopropanol. A light yellow product was obtained.

Yield = 16.7 g = 65%
m.p. = 138° C.

| 4-Chlorobenzalphthalide Spectra Data | | |
| --- | --- | --- |
| $\lambda_{max}$ = 298 nanometers | K = 249 | CHCl$_3$ Solvent |
| $\lambda_{max}$ = 311 nanometers | K = 257 | |
| $\lambda_{max}$ = 340 nanometers | K = 303 | |

| SUNSCREEN DATA | | |
| --- | --- | --- |
| Concentration | Erythemal Transmission | Tanning Transmission |
| 3% | 0.39% | 1.13% |

EXAMPLE 3

3-Methoxybenzalphthalide 20.0 g (0.12 mole) 3-methoxyphenyl acetic acid
14.8 g (0.1 mole) phthalic anhydride
0.2 g Fused sodium acetate Above materials were heated to 230°–240° C. and held there for 3 hrs.; 1.7 ml of water was collected in the trap. Mixture cooled to 90° C. and added to 500 ml isopropanol. After cooling to room temperature the crystals were filtered off. A second crystallization from 500 ml isopropanol yielded a very light yellow solid.

Yield = 17.1 g = 69%
m.p. = 138° C.

| 3-Methoxybenzalphthalide Spectra Data | | |
| --- | --- | --- |
| $\lambda_{max}$ = 300 nanometers | K = 218 | CHCl$_3$ solvent |
| $\lambda_{max}$ = 343 nanometers | K = 244 | |

| SUNSCREEN DATA | | |
| --- | --- | --- |
| Concentration | Erythemal Transmission | Tanning Transmission |
| 3% | 0.79% | 1.31% |

EXAMPLE 4

4-Methylbenzalphthalide 10 g (0.067 mole) 4-methylphenyl acetic acid
12.3 g (0.083 mole) phthalic anhydride
0.2 g Fused sodium acetate Above materials were heated to 240° C. for 3 hrs. At the end of this period 1.2 ml of water was collected in a trap. The mixture was cooled to 90° C. and poured into 500 ml isopropanol. Solids were removed under vacuum and recrystalized from 300 ml hot isopropanol.

Yield = 11.4 g = 72%
m.p. = 123° C.
Color = yellow

| 4-Methylbenzalphthalide Spectra Data | | |
| --- | --- | --- |
| $\lambda_{max}$ = 301 nanometers | K = 224 | CHCl$_3$ Solvent |
| $\lambda_{max}$ = 312 nanometers | K = 228 | |
| $\lambda_{max}$ = 344 nanometers | K = 264 | |

| SUNSCREEN DATA | | |
| --- | --- | --- |
| Concentration | Erythemal Transmission | Tanning Transmission |
| 3% | 0.67% | 0.82% |

EXAMPLE 5

Benzal-3-Methyl Phthalide 16.3 g phenyl acetic acid
16.2 g 3-methyl phthalic anhydride
0.2 g sodium acetate fused The above materials were heated at 250° C. for 2 hrs. in a nitrogen atmosphere. At the end of the reaction period the charge was cooled to 75°–80° C. and added to 100 g isopropanol. After boiling the solution was filtered and cooled to room temperature. A small amount of solids precipitates out (2.1 g). After drying this material had a melting point above 360° C. (Compound #1). The isopropanol solution was cooled in a dry ice bath to obtain a second crop; (4.2 g) this material had a melting point of 357° C. (Compound #2). After concentrating the isopropanol to about one-tenth its volume, 0.2 g of product was obtained; melting point 150° C. (Compound #3).

| U.V. Spectro Data (Isopropanol is the Solvent) | | |
| --- | --- | --- |
| compound #1 | 343 nanometers | K = 83 |
| | 308 nanometers | K = 72 |
| | 294 nanometers | K = 75.6 |
| Compound #2 | 343 nanometers | K = 89 |
| | 308 nanometers | K = 80 |
| | 294 nanometers | K = 88 |
| Compound #3 | 343 nanometers | K = 95.4 |
| | 308 nanometers | K = 81.4 |
| | 294 nanometers | K = 83.4 |

No attempt was made to elucidate the structure of these three compounds. The commercial product would contain the mixture of all three compounds.

EXAMPLE 6

3-Methoxy Benzal-3-Methyl Phthalide

Another example prepared from 3-methyl phthalic anhydride and 3-methoxy phenyl acetic acid using the method outlined above. The isomers were not isolated, the U.V. data was determined on the mixture.

| U.V. Spectro Data (Isopropanol Solvent) | |
|---|---|
| 293 nanometers | K = 67.0 |
| 303 nanometers | K = 64.3 |
| 347 nanometers | K = 78.5 |

The effectiveness of a sunscreening agent can also be determined by dividing the absorbance at the maximum peak between 290 and 315 by the concentration in grams per liter. This is known as the "K" value of a sunscreening agent. The higher the "K" value, the better the sunscreening ability and the lower the amount of material needed for protection from erythemal rays of the sun. In other words, from the "K" value the amount of sunscreening agent necessary for protection of the sun ultraviolet radiation can be determined and used in any cosmetically acceptable base preparation.

These examples demonstrate that the materials of this invention in even small quantities are extremely effective broad spectrum sun screen agents.

It is of significance that in the materials tested in Examples 2 through 4 the position of the substituent was important as regards activity.

4-hydroxybenzalphthalide also has demonstrated sun screen effectiveness.

Mixtures of the materials of this invention can be employed where desirable.

The advantages of this invention will be apparent to the skilled in the art. Improved, highly effective, novel, broad spectrum sun screens are made available.

It will be understood that this invention is not limited to the specific examples which have been offered as particular embodiments, and that modifications can be made without departing from the spirit thereof.

What is claimed is:

1. A composition adapted for application to the human skin comprising a cosmetic oil carrier containing distributed therein from an effective amount to provide substantial protection against erythemal and tanning radiation up to the limit of solubility therein of a benzalphthalide.

2. The composition of claim 1, in which the benzalphthalide has the formula

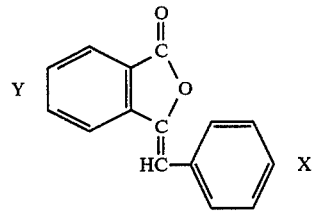

wherein X and Y are selected from the group consisting of hydrogen, methyl, ethyl, methoxy, hydroxy and chloro.

3. The composition of claim 2 in which the benzalphthalide is 4-chlorobenzalphthalide.

4. The composition of claim 2 in which the benzalphthalide is 4-methylbenzalphthalide.

5. The composition of claim 2 in which the benzalphthalide is 3-methoxybenzalphthalide.

6. The composition of claim 2 in which the benzalphthalide is benzal-3-3-methyl phthalide.

7. The composition of claim 2 in which the benzalphthalide is 3-methoxy benzal-3-methyl phthalide.

8. The composition of claim 1 in which the benzalphthalide is benzalphthalide.

9. A method of protecting the human skin from the effects of erythema and tanning radiation in sunlight which comprises applying to said skin a benzalphthalide contained in a cosmetic oil carrier.

10. The method of claim 9, in which the benzalphthalide has the formula

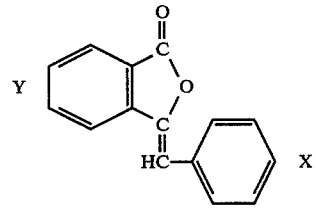

wherein X and Y are selected from the group consisting of hydrogen, methyl, ethyl, methoxy, hydroxy and chloro.

11. The method of claim 10 in which the benzalphthalide is 4-chlorobenzalphthalide.

12. The method of claim 10 in which the benzalphthalide is 4-methylbenzalphthalide.

13. The method of claim 10 in which the benzalphthalide is 3-methoxybenzalphthalide.

14. The method of claim 10 in which the benzalphthalide is benzal-3-methyl phthalide.

15. The method of claim 10 in which the benzalphthalide is 3-methoxy benzal-3-methyl phthalide.

16. The method of claim 10 in which the benzalphthalide is benzalphthalide.

17. A method of protecting the human skin from the effects of erythema and tanning radiation in sunlight which comprises applying to said skin a benzalphthalide contained in a carrier, the benzalphthalide being distributed in the carrier in an effective amount to supply the protection to the human skin.

18. The method of claim 17 in which the benzalphthalide is present in the carrier in the range of from about 1 to about 8 wt.%.

* * * * *